(12) United States Patent
Essayem et al.

(10) Patent No.: US 9,464,025 B2
(45) Date of Patent: Oct. 11, 2016

(54) METHOD FOR PREPARING LEVULINIC ACID ESTERS

(71) Applicants: CENTRE NATIONAL DE LA RECHERCHE SCIENTIFIQUE (C.N.R.S), Paris (FR); UNIVERSITE CLAUDE BERNARD LYON 1, Villeurbanne (FR)

(72) Inventors: Nadine Essayem, Saint Just Chaleyssin (FR); Gilbert Sapaly, Lyons (FR); Marion Eternot, Ecully (FR); Franck Rataboul, Lyons (FR)

(73) Assignees: CENTRE NATIONAL DE LA RECHERCHE SCIENTIFIQUE (C.N.R.S.), Paris (FR); UNIVERSITE CLAUDE BERNARD LYON 1, Villeuranne (FR)

( * ) Notice: Subject to any disclaimer, the term of this patent is extended or adjusted under 35 U.S.C. 154(b) by 1 day.

(21) Appl. No.: 14/410,905

(22) PCT Filed: Jun. 28, 2013

(86) PCT No.: PCT/EP2013/063593
§ 371 (c)(1),
(2) Date: Dec. 23, 2014

(87) PCT Pub. No.: WO2014/001486
PCT Pub. Date: Jan. 3, 2014

(65) Prior Publication Data
US 2015/0203435 A1    Jul. 23, 2015

Related U.S. Application Data

(60) Provisional application No. 61/666,294, filed on Jun. 29, 2012.

(30) Foreign Application Priority Data

Jul. 2, 2012 (FR) .................................. 12 56334

(51) Int. Cl.
*C07C 67/00* (2006.01)
*C10L 1/16* (2006.01)
*C10L 1/19* (2006.01)

(52) U.S. Cl.
CPC .............. *C07C 67/00* (2013.01); *C10L 1/1608* (2013.01); *C10L 1/19* (2013.01); *C10L 2200/0469* (2013.01); *C10L 2270/023* (2013.01); *C10L 2270/026* (2013.01); *Y02P 20/544* (2015.11)

(58) Field of Classification Search
CPC ... C07C 67/00; C07C 69/716; C10L 1/1608; C10L 1/19; C10L 2200/0469; C10L 2270/023; C10L 2270/026; Y02P 20/544
USPC ............................................. 560/174; 44/388
See application file for complete search history.

(56) References Cited

U.S. PATENT DOCUMENTS

2003/0233011 A1* 12/2003 Fagan ..................... C07C 67/04
560/174

FOREIGN PATENT DOCUMENTS

WO    03/085071 A1    10/2003
WO    2005/070867 A1    8/2005

OTHER PUBLICATIONS

"Synthesis and Applications of Alkyl Levulinates" ACS Sustainable Chemistry and Engineering, 2014, 2, p. 1338-1352.*

(Continued)

*Primary Examiner* — Jafar Parsa
*Assistant Examiner* — Amy C Bonaparte
(74) *Attorney, Agent, or Firm* — Young & Thompson

(57) ABSTRACT

A method for preparing at least one ester of levulinic acid from a biomass includes steps of impregnating the biomass by an organic or inorganic acid, and putting the acidified biomass in contact with a supercritical fluid including at least one olefin.

14 Claims, 2 Drawing Sheets

(56) References Cited

OTHER PUBLICATIONS

"Conversion of biomass platform molecules into fuel additives and liquid hydrocarbon fuels" Green Chemistry, 2014, 16, p. 516-547.*
Franck Rataboul et al.: "Cellulose Reactivity in Supercritical Methanol in the Presence of Solid Acid Catalysts: Direct Synthesis of Methyl-levulinate", Industrial & Engineering Chemistry Research, vol. 50, No. 2, Jan. 19, 2011, pp. 799-805, XP055055197, ISSN: 0888-5885, DOI: 10.1021/ie101616e p. 800, paragraph 2-, figure 1-.
International Search Report, dated Sep. 4, 2013, from corresponding PCT application.
FR Search Report, dated Mar. 6, 2013, from corresponds FR application.

\* cited by examiner

METHOD FOR PREPARING LEVULINIC ACID ESTERS

FIELD OF THE INVENTION

The present invention relates to a method for preparing at least one ester of levulinic acid.

The invention also relates to a composition comprising at least one ester of levulinic acid and at least one olefin.

BACKGROUD OF THE INVENTION

Levulinic acid, and most particularly its esters, are intermediates with a very strong potential and represent key products within tomorrow's biorefineries.

Esters of levulinic acid are known as fuel additives but also as important synthesis intermediates.

Several methods for preparing esters of levulinic acid have been described.

WO 2005/070867 describes a method using reactive extraction during which an aqueous solution of levulinic acid, obtained in a first step of acid hydrolysis of a biomass, is put into contact with an alcohol including at least four carbon atoms. This alcohol, non-miscible with water, acts as an esterification reagent but also as a solvent for extracting levulinate.

WO 2003/085071 describes the obtaining of esters of levulinic acid by esterification of olefins and of aqueous solutions containing levulinic acid. These aqueous solutions of levulinic acid stem from a first step of acid hydrolysis of diverse biomasses in the presence of water and of an acid catalyst.

The methods of the state of the arts necessarily comprise two steps including a step consisting in obtaining an aqueous solution of levulinic acid by acid hydrolysis of a biomass.

However, resorting to such a step causes different problems, including generation of aqueous acid effluents, difficulty in controlling the selectivity of the transformation or further problems of corrosion of the installations.

Moreover, a method for preparing methyl levulinate by reaction of cellulose with a methanol under supercritical conditions in the presence of an acid catalyst has been described (Rataboul et al., *Ind. Eng. Chem. Res,* 2011, Vol. 50, no. 2, pp. 799-805). However, the described method comprises the application of a liquid phase, thereby requiring a step for separating the phases in order to be able to recover methyl levulinate. Further, the presence of methanol generates the production of water which may thus affect the catalytic activity of the acid catalyst.

SUMMARY OF THE INVENTION

Thus, a first object of the invention is to propose a method for preparing esters of levulinic acid which provides a solution to all or part of the problems of the methods of the state of the art.

Another object of the invention is to propose a method for preparing esters of levulinic acid which is easy to apply, while having a satisfactory yield, and thus being able to be transposed to an industrial scale.

Another object of the invention is to propose a method for preparing esters of levulinic acid in the absence of water or in the presence of a small amount of water, giving the possibility of limiting or even suppressing the obtaining of undesirable reaction byproducts, such as for example humins.

Another object of the invention is to propose a method for preparing esters of levulinic acid which may appear as a liquid composition.

The object of the present invention is a method for preparing at least one ester of levulinic acid from a biomass comprising:
 i) impregnating the biomass by means of an organic or inorganic acid;
 ii) putting the acidified biomass in contact with a supercritical fluid comprising at least one olefin.

According to the invention, an ester of levulinic acid is a compound of formula (I)

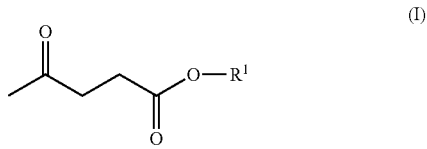

wherein $R^1$ represents a branched or linear, cyclic or bicyclic $C_2$-$C_{20}$ alkyl group.

Advantageously, $R^1$ represents a linear or branched $C_2$-$C_6$ alkyl group.

Advantageously, the ester of levulinic acid is selected from ethyl levulinate, propyl levulinate or butyl levulinate.

Still more advantageously, the ester of levulinic acid is butyl levulinate, notably sec-butyl levulinate.

By biomass is meant any material comprising at least one carbohydrate.

By biomass is also meant any material comprising a polysaccharide.

According to the invention, the biomass may be a ligno-cellulose biomass.

The term of ligno-cellulose biomass (LCB) encompasses several products present in variable amounts according to their origin: cellulose, hemicellulose, lignin. The carbohydrate portion of lignocellulose is made of hemicellulose and cellulose. These are polymers of sugars (pentoses and hexoses). Lignin is a macromolecule rich in phenolic units.

According to the invention, ligno-cellulose biomass may notably comprise wood or plant wastes. Out of the non-limiting examples of ligno-cellulose biomass material are residues from farms, notably straw, grasses, stems, cores, shells, forest residues, notably first thinning products, barks, sawdusts, shavings, scraps, forestry products, dedicated cultures, notably short rotation coppices, residues of the agri-food industry, notably residues from the cotton, bamboo, sisal, banana, maize, *Panicum virgatum*, alfalfa, coconut, bagasse industry, domestic organic wastes, wastes from wood transformation facilities, used building wood, paper, either recycled or not.

According to the invention, the ligno-cellulose biomass may be used in its crude form, i.e. in its integrality of these three constituents: cellulose, hemicellulose and lignin. The crude biomass generally appears as sawdust or powder. Generally it is milled or shredded to allow its transport.

According to the invention, the biomass is cellulose and the average particle size ranges from 1 to 50 µm, preferably from 10 to 30 µm.

According to the invention, the biomass is a resinous wood or hardwood and the average particle size ranges from 0.5 to 5 mm, preferably from 1 to 2 mm. As an example of wood, mention may be made of spruce.

Advantageously, the biomass appears as a solid, notably in a dried or dehydrated form.

According to the invention, the impregnation of the biomass is achieved by means of an aqueous solution of an organic or inorganic acid.

According to the invention, the organic acid may be a carboxylic acid.

According to the invention, the nature of the carboxylic acid should be selected in order to pre-treat the biomass satisfactorily.

According to the invention, the carboxylic acid concentration of the medium should be sufficiently large for pre-treating the biomass satisfactorily.

Indeed, generally, the nature and the concentration of the medium of carboxylic acids which may be released by the biomass does not give the possibility of obtaining sufficient acidification of the biomass required for treatment with a supercritical fluid comprising at least one olefin.

According to the invention, the acid may be an inorganic acid.

According to the invention, the inorganic acid may be selected from phosphoric acid, hydrochloric acid or sulfuric acid.

Advantageously, the inorganic acid is sulfuric acid.

According to the invention, the impregnation of the biomass may be accomplished under impregnation conditions with nascent humidity.

Unlike complete immersion of the biomass in the aqueous solution of an organic or inorganic acid, impregnation conditions with nascent humidity may notably correspond to a volume of aqueous acid solution close to or equivalent to the porous volume of the biomass to be impregnated.

According to the invention, the impregnation of the biomass may be accomplished by dry impregnation or by putting the biomass in contact with an acid vapor.

Generally, according to the invention, the impregnation duration of the biomass may range from a few minutes to several hours, for example from 1 to 5 h.

Surprisingly, it was found that the structure of the acidified biomass of the method according to the invention is not modified.

Thus, for example, the cellulose of the acidified biomass has the same characteristics as a non-impregnated cellulose.

The method according to the invention thus gives the possibility of obtaining the whole of the available biomass so as to put it in contact with the supercritical fluid, while avoiding degradations and/or modifications of all or part of this biomass.

According to the invention, the supercritical fluid comprises an olefin alone or as a mixture.

According to the invention, the supercritical fluid of step ii) is obtained by applying temperature and pressure conditions close to or greater than the critical temperature and pressure of the fluid comprising the olefin or of the olefin as a fluid or greater than the critical point of the fluid comprising the olefin or of the olefin as a fluid.

Thus, for each olefin alone or as a mixture, one skilled in the art may determine the supercritical conditions of temperature and pressure of the fluid.

According to the invention, the supercritical fluid comprises at least one organic fluid. Advantageously, the organic fluid comprises at least one organic compound.

By olefin is meant any compound of formula (II)

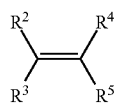

(II)

wherein, $R^2$, $R^3$, $R^4$ and $R^5$, either identical or different, represent independently a hydrogen or a $C_1$-$C_6$ alkyl group.

Advantageously, the supercritical fluid comprises an olefin selected from ethylene, propene or butene.

Even more advantageously, the supercritical fluid comprises butene, notably but-2-ene.

Advantageously, the supercritical fluid is a dense or very dense supercritical fluid.

Advantageously, an additional increase of the pressure on the supercritical fluid is applied in order to increase the density thereof.

One skilled in the art will know how to apply the pressure conditions required for obtaining a dense or very dense supercritical fluid, notably depending on the nature of the organic compound, for example according to the olefin applied.

For example, for butene, a pressure from 40 to 150 bars, preferably from 50 to 100 bars will generally be applied.

Thus, by increasing the density of the supercritical fluid, the yield of the method according to the invention is improved.

According to the invention, an additional step for drying the acidified biomass may be carried out.

Advantageously, the drying is carried out at a low temperature, preferably at room temperature.

Thus, by this low temperature drying, the risks of degradation of the biomass are limited, or even suppressed, unlike with drying by heating.

Advantageously, the drying of the method according to the invention may be carried out in vacuo or at a reduced pressure.

According to the invention, the method may be applied in any continuous or semi-continuous device adapted to catalytic reaction of a compound in the presence of a supercritical fluid. An exemplary device is described in Salinas et al. (Salinas et al., Ing. Eng. Chem. Res, 2004, 43, 6355-6362).

Another object of the present invention relates to a composition comprising at least one ester of levulinic acid and at least one olefin.

The composition according to the invention advantageously appears in a liquid form or in an oily form.

The definitions and preferred characteristics of the ester of levulinic acid and of the olefin shown for the method according to the invention apply to the composition according to the invention.

Thus, the ester of levulinic acid is selected from ethyl levulinate, propyl levulinate or butyl levulinate.

Advantageously, the ester of levulinic acid is butyl levulinate, notably sec-butyl levulinate.

Thus, the olefin is selected from ethylene, propene or butene.

Advantageously, the olefin is butene, notably but-2-ene.

According to the invention, the ester of levulinic acid of the composition according to the invention is derived from an acidified biomass by impregnation of this biomass by means of an organic or inorganic acid followed by putting it into contact with a supercritical fluid comprising at least one olefin.

In particular, the ester of levulinic acid is preferably prepared by applying the method according to the invention.

The definitions and preferred characteristics of the biomass and of the acid shown for the method according to the invention apply to the composition according to the invention.

Thus, the biomass may be a lignocellulose biomass.

The term of lignocellulose biomass (LCB) encompasses several products present in variable amounts according to their origin: cellulose, hemicellulose, lignin. The carbohydrate portion of the lignocellulose is made of hemicellulose and cellulose. These are polymers of sugars (pentoses and hexoses). Lignin is a macromolecule rich in phenolic units.

According to the invention, the lignocellulose biomass may notably comprise wood or plant wastes. Other non-limiting examples of lignocellulose biomass material are the residues of farms, notably straw, grasses, stems, cores, shells, forest residues, notably first thinning products, barks, sawdusts, shavings, scraps, forestry products, dedicated cultures, notably short rotation coppices, residues of the agri-feed industry, notably residues of the cotton, bamboo, sisal, banana, maize, *Panicum virgatum*, alfalfa, coconut, bagasse industry, domestic organic wastes, wastes from wood transformation facilities, used building wood, paper, either recycled or not.

According to the invention, the lignocellulose biomass may be used in its crude form, i.e. in its integrality of these three constituents: cellulose, hemicellulose and lignin. The crude biomass generally appears as sawdust or powder. Generally, it is milled or shredded for allowing its transport.

Thus, the organic acid may be a carboxylic acid.

Thus, the acid may be an inorganic acid. According to the invention, the inorganic acid may be selected from phosphoric acid, hydrochloric acid or sulfuric acid. Advantageously, the inorganic acid is sulfuric acid.

The composition according to the invention may advantageously be used as a basis for fuel either directly or as a mixture, for example as oxygenated additives for diesel or gasoline fuels.

DETAILED DESCRIPTION OF THE INVENTION

Different aspects of the invention are illustrated by the examples which follow. These examples are given as an indication, without any limitation.

In these examples, the olefin is a mixture of cis and trans but-2-ene (45% cis and 55% trans), conditioned in a cylinder equipped with a plunger tube and pressurized with 8 bars of He (helium).

The critical coordinates of cis but-2-ene and of trans but-2-ene are the following:

|  | Critical T (° C.) | Critical P (bars) |
|---|---|---|
| Trans-2-$C_4^=$ | 155.45 | 41.03 |
| cis-2- $C_4^=$ | 162.45 | 42.04 |

Figure 1:
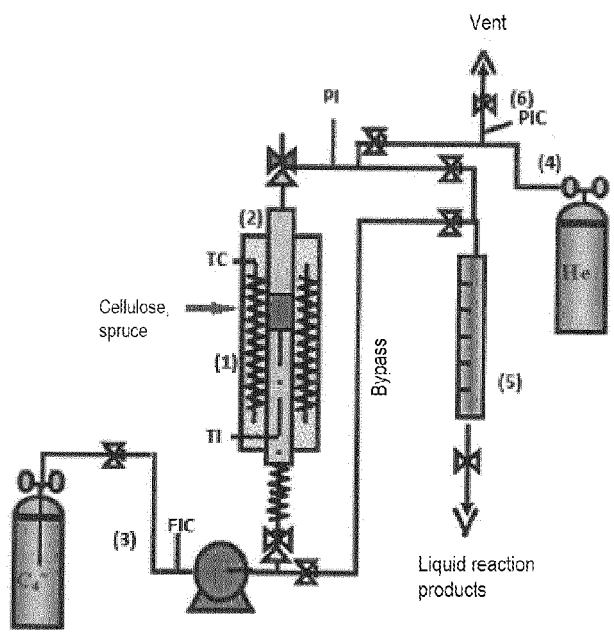
FIG. 1 illustrates the device used for the process of the invention.

The reaction occurs in the device as illustrated in FIG. 1, comprising:
1. reaction oven,
2. tubular reactor containing a bed of solid biomass,
3. a supply (cylinder with a plunger tube and pump) of the liquid olefin,
4. helium supply,
5. condenser downstream from the reaction oven,
6. pressure regulation.

The reaction was applied in a semi-continuous reactor wherein the biomass was put into contact with the olefin in a dense phase at a high temperature and high pressure. By dense phase at a high temperature and at a high pressure, is meant greater temperatures and pressure, close to or greater than the critical pressure and temperature of the olefin, preferably a temperature comprised between 150-200° C. and a pressure comprised between 40-150 bars.

Characterization Techniques:

the liquid products were analyzed by gas chromatography coupled with a mass spectrometer.

Expression of the Results:

The weight yield of sec-butyl levulinate was calculated according to the following equation:

$$\text{Weight yield for levulinate} = 100 \times (m \text{ levulinate})/m \text{ (dry carbohydrate)}$$

wherein m (levulinate) represents the produced mass of sec-butyl levulinate and m (dry carbohydrate) represents the mass of dry biomass.

The molar yield of sec-butyl levulinate (corrected from the number of carbon atoms) was calculated according to the following equation:

$$\text{Molar yield of levulinate} = 100 \times (nb(\text{mol of levulinate})*5)/nb(\text{mol of GPU})$$

wherein nb (mol levulinate) represents the number of moles of sec-butyl levulinate produced and nb (mol of GPU) represents the number of moles of glucose or pentose units (GPUs) contained in the biomass loaded into the reactor.

EXAMPLE 1

Preparation of Sec-Butyl Levulinate from Cellulose or Spruce and from but-2-Ene Under Supercritical Conditions The cellulose is microcrystalline cellulose Sigmacell from Aldrich, The cellulose was impregnated in the following way: 2 g of cellulose were impregnated with nascent humidity with an aqueous solution:
of acetic acid (10 or 30% by weight); or
of phosphoric acid (1% by weight); or
of sulfuric acid (1% by weight).

The acidified cellulose was then dried in vacuo at room temperature.

The acidified cellulose is not affected by this impregnation.

Figure 2:
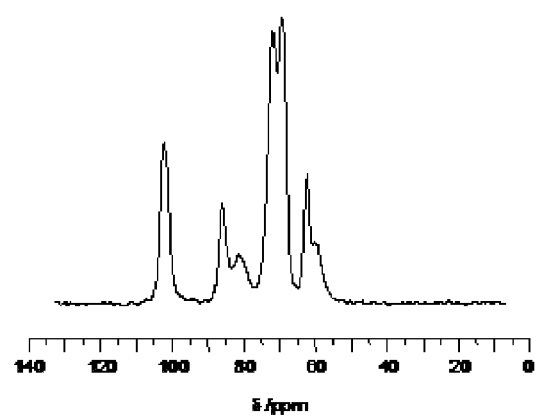
FIG. 2 illustrates the $^{13}$C MAS-NMR spectrum of the non-impregnated cellulose.

FIG. 2 illustrates the $^{13}$C MAS-NMR spectrum of the non-impregnated cellulose.

Figure 3:
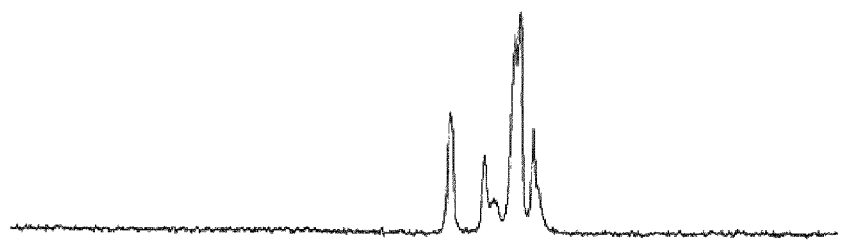
FIG. 3 illustrates the $^{13}$C MAS-NMR spectrum of the cellulose impregnated by means of a sulfuric acid solution at 1% by weight.

FIG. 3 illustrates the $^{13}$C MAS-NMR spectrum of the cellulose impregnated by means of a sulfuric acid solution at 1% by weight.

Figure 4:
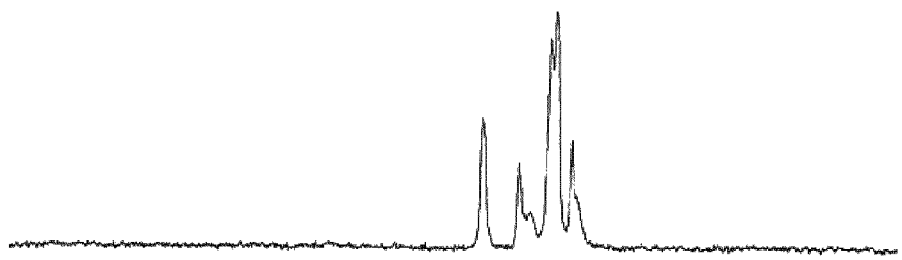
FIG. 4 illustrates the $^{13}$C MAS-NMR spectrum of the cellulose impregnated by means of a phosphoric acid solution at 1% by weight.

FIG. 4 illustrates, shows the $^{13}$C MAS-NMR spectrum of the cellulose impregnated by means of a phosphoric acid solution at 1% by weight.

Thus, the three spectra of FIGS. 2, 3 and 4 are identical.

This shows that the impregnation process of the method according to the invention does not deteriorate or modify the structure of the biomass used, thereby giving the possibility that the whole of this biomass is available for being put into contact with the supercritical fluid.

2 g of acidified cellulose are then placed in a tubular reactor. The biomass was maintained in the central portion of the reactor by means of quartz wool plugs. The upper and lower portions of the reactor were filled with silicon carbide (pd=0.5 mm).

The reactor was connected to the continuous test, pressurized to the desired pressure by means of helium. Liquid but-2-ene is pumped by means of an HPLC type pump at a flow rate of 1 cm$^3$/min in order to wet the biomass beforehand and then the flow rate was reduced to 0.1 cm$^3$/min.

The temperature of the reactor was then gradually increased up to the reaction temperature.

The liquid products were recovered at the outlet of the test at ambient pressure and room temperature. After total evaporation of but-2-ene, the liquid sample was weighed and analyzed by gas chromatography.

The results obtained according to the nature of the acid used during the pre-treatment and on the reaction temperature are gathered in Table 1.

The cellulose pretreated by the means of sulfuric acid, followed by the reaction with but-2-ene at 170° C. but at decreasing pressures 100 bars (test 4: olefin phase SC high pressure), 50 bars (test 5: olefin close to the critical point), 30 bars (test 6: olefin gas phase at high pressure), produces decreasing amounts of liquid products at room temperature.

The highest yield is obtained by reacting the cellulose with a flow of olefin in an SC phase at high pressure, a dense SC phase (test 4). Close to the critical point (test 5), the transformation of the cellulose is more limited just like the levulinate yield.

The olefin used in a gaseous phase at a same temperature (test 6), does not allow liquefaction of the cellulose. Finally, when the cellulose, pretreated with sulfuric acid, is treated under a flow of liquid butene at a high pressure (test 7), the transformation of the cellulose into levulinate is not effective.

These tests show the importance of using a flow of butene in a supercritical phase, for transforming the cellulose into levulinate in a single step.

TABLE 1

| Test No. | Pretreatment cellulose | T (° C.) | P (bars) | Recovered liquid m (g) | Recovered sold m (g) | Recovered solid color | Yield of sec-butyl levulinate (wt %) | Yield of sec-butyl levulinate (mol %) |
|---|---|---|---|---|---|---|---|---|
| 1 | without | 170 | 100 | 0 | 2 | Cream | — | — |
| 2 | H$_3$PO$_4$ (1 wt %) | 170 | 100 | 0.23 | 1.35 | Brown | 0.8 | 0.6 |
| 3 | H$_2$SO$_4$ (1 wt %) | 150 | 100 | 0.8 | 0.94 | Dark brown | 13.3 | 10.4 |
| 4 | H$_2$SO$_4$ (1 wt %) | 170 | 100 | 1.1 | 0.94 | Dark brown | 15.7 | 13.5 |
| 5 | H$_2$SO$_4$ (1 wt %) | 170 | 50 | 0.17 | 1.19 | Dark brown | 2.2 | 1.9 |
| 6 | H$_2$SO$_4$ (1 wt %) | 170 | 30 | 0.02 | 1.15 | Dark brown | 0.7 | 0.6 |
| 7 | H$_2$SO$_4$ (1 wt %) | 130 | 100 | 0.09 | 1.25 | Dark brown | 0.7 | 0.6 | wt % = percent by weight

The results show that in the absence of any pretreatment (test 1), the reaction conducted for 6 h at 170° C. and at 100 bars (temperature and pressure greater than the critical temperature and pressure of but-2-ene), no liquid product at ambient pressure and room temperature is obtained.

This shows the importance of the pretreatment by impregnation of the biomass with an organic or inorganic acid.

A treatment of the cellulose with an aqueous solution of 1% phosphoric acid followed by a treatment with a flow of but-2-ene at 170° C., allows detection of the liquid products at the outlet of the test. More than one quarter of the cellulose was de-polymerized. The analysis of the liquid products recovered by GC-MS show the formation of sec-butyl levulinate, of sec-butyl formate and of furfural as majority products. The yield of sec-butyl levulinate is 0.6% (test 2). The cellulose recovered at the end of the reaction at 170° C. has a brown coloration.

The pretreatment of the cellulose with sulfuric acid, followed by the reaction with but-2-ene at 150 or 170° C., 100 bars (tests 3 and 4), allows depolymerization of the cellulose and produces a significant amount of products liquid at ambient T and P. The mass yield of sec-butyl levulinate is 15.7% (molar yield of 13.5%).

EXAMPLE 2

Preparation of Sec-Butyl Levulinate from Spruce and from but-2-Ene Under Supercritical Conditions The spruce has the following composition:

| Glucan | Xylan | Mannan | Galactan | Arabinan | Lignin |
|---|---|---|---|---|---|
| 46.2% | 8.2% | 14.2% | 2.5% | 1.2% | 26.1% |

The pretreatments and the reaction were conducted as in example 1. The spruce was milled and sifted.

The results obtained according to the nature of the acids used during the pretreatment and on the reaction temperature are gathered in table 2.

TABLE 2

| Tests | spruce pretreatment | T(° C.) | P (bars) | mass of initial spruce (g) | recovered liquid mass (g) | Recovered solid mass (g) | recovered solid color | yield of sec-butyl levulinate (wt %) | yield of sec-butyl levulinate (%) |
|---|---|---|---|---|---|---|---|---|---|
| 1 | without | 170 | 100 | 1 | 0 | 1 | beige | — | — |
| 2 | $H_3PO_4$ (1 wt %) | 170 | 100 | 1.24 | 0.34 | 0.78 | Dark brown | 3.4 | 2.8 |
| 3 | $H_2SO_4$ (1 wt %)) | 170 | 100 | 1.68 | 1.24 | 0.7 | Black | 8.8 | 7.7 | wt % = percentage by weight

Without any pretreatment of the spruce, no liquid product at ambient P and T is formed by reaction with the sec-but-2-ene under SC conditions (170° C., 100 bars), for 6 h (test 1). The recovered spruce after reaction is not very colored, it has a slight beige hue.

Following the acidification of the spruce biomass with phosphoric acid (1% by weight), the reaction with but-2-ene at 170° C. allows depolymerization of the spruce (test 2). The solid biomass has a dark brown color after reaction. The analysis of the liquid formed shows a weight yield of sec-butyl levulinate of 3.4% calculated on the carbohydrate portion of the spruce.

Following a pretreatment with sulfuric acid and reaction with but-2-ene under supercritical conditions, the analysis of the recovered liquid, after evaporation at ambient temperature and pressure, allows an 8.8% yield of sec-butyl levulinate (test 3). The recovered solid biomass after reaction has a black coloration.

These tests confirm the importance of the pretreatment of the biomass by impregnation with an organic or inorganic acid and as well as the importance of the supercritical conditions of the fluid comprising the olefin.

The invention claimed is:

1. A method for preparing at least one ester of levulinic acid from a biomass comprising:
   i) impregnation of the biomass with an organic or inorganic acid; and
   ii) putting the acidified biomass in contact with a supercritical fluid comprising at least one olefin.

2. The method according to claim 1, wherein the biomass is a lignocellulose biomass.

3. The method according to claim 1, wherein the biomass is in a particulate form.

4. The method according to claim 1, wherein the impregnation of the biomass accomplished with an aqueous solution of an organic or inorganic acid.

5. The method according to claim 1, wherein the acid is an inorganic acid.

6. The method according to claim 1, wherein the impregnation of the biomass is carried out under impregnation conditions with nascent humidity, which corresponds to a volume of an aqueous acid solution close to or equivalent to the porous volume of the biomass to be impregnated.

7. The method according to claim 1, wherein the supercritical fluid is obtained by applying temperature and pressure conditions close to or greater than the critical temperature and pressure of a fluid comprising at least one olefin or of the olefin as a fluid.

8. The method according to claim 1, wherein the supercritical fluid is an organic fluid.

9. The method according to claim 8, wherein the supercritical fluid comprises butene.

10. The method according to claim 1, wherein the supercritical fluid is a dense supercritical fluid.

11. The method according to claim 1, further comprising, after step (i) and before step (ii), drying the acidified biomass.

12. The method according to claim 11, wherein the drying is carried out at low temperature.

13. The method according to claim 5, wherein the acid is sulfuric acid.

14. The method according to claim 8, wherein the supercritical fluid comprises but-2-ene.

* * * * *